US008063264B2

(12) United States Patent
Spearman et al.

(10) Patent No.: US 8,063,264 B2
(45) Date of Patent: Nov. 22, 2011

(54) HEMOSTATIC MEDIA

(76) Inventors: Michael Spearman, The Woodlands, TX (US); Keith Roberts, White Bear Lake, MN (US); Majid Zia, St. Paul, MN (US)

(*) Notice: Subject to any disclaimer, the term of this patent is extended or adjusted under 35 U.S.C. 154(b) by 220 days.

(21) Appl. No.: 11/510,505

(22) Filed: Aug. 25, 2006

(65) Prior Publication Data

US 2007/0060856 A1   Mar. 15, 2007

Related U.S. Application Data

(60) Provisional application No. 60/711,844, filed on Aug. 26, 2005.

(51) Int. Cl.
*A61F 13/00* (2006.01)
*A61L 15/16* (2006.01)
*D04H 1/00* (2006.01)

(52) U.S. Cl. ............. 602/48; 424/443; 424/446; 442/50

(58) Field of Classification Search .................... 602/48; 424/445, 443, 444, 446, 447, 448, 449; 442/4, 442/50, 51, 58, 60, 152; 604/6.01, 6.02, 604/6.04

See application file for complete search history.

(56) References Cited

U.S. PATENT DOCUMENTS

| 4,128,612 A * | 12/1978 | Roth ............................. 264/126 |
| 4,468,428 A * | 8/1984 | Early et al. ..................... 428/221 |
| 4,878,908 A * | 11/1989 | Martin et al. ................. 623/1.54 |
| 5,472,600 A * | 12/1995 | Ellefson et al. ............... 210/317 |
| 5,759,570 A * | 6/1998 | Arnold .......................... 424/443 |
| 6,689,166 B2 * | 2/2004 | Laurencin et al. ......... 623/11.11 |
| 6,824,718 B2 * | 11/2004 | Eitzman et al. ............... 264/101 |
| 7,309,498 B2 * | 12/2007 | Belenkaya et al. .......... 424/443 |
| 2004/0005434 A1 * | 1/2004 | Calhoun et al. ................. 428/91 |
| 2004/0015115 A1 * | 1/2004 | Sinyagin ......................... 602/42 |
| 2005/0143810 A1 * | 6/2005 | Dauner et al. ............... 623/2.12 |
| 2006/0013863 A1 * | 1/2006 | Shalaby et al. ............... 424/443 |

* cited by examiner

*Primary Examiner* — Patricia Bianco
*Assistant Examiner* — Ophelia Hawthorne
(74) *Attorney, Agent, or Firm* — Jacobson & Johnson LLC

(57) ABSTRACT

A wound dressing and a method for enhancing the clotting comprising a plurality of hydrophilic microfibers bonded to each other to form a mat with the plurality of microfibers having a pore size sufficiently small to inhibit wicking platelets from a wound into the microfibers so that when applied to a wound the blood coagulates and the microfibers remain external to the wound.

23 Claims, 1 Drawing Sheet

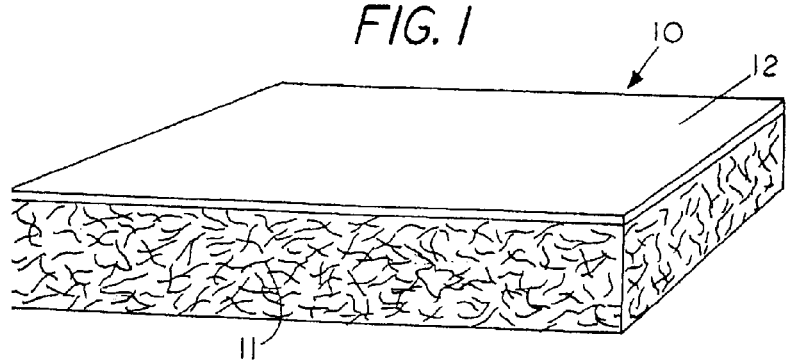
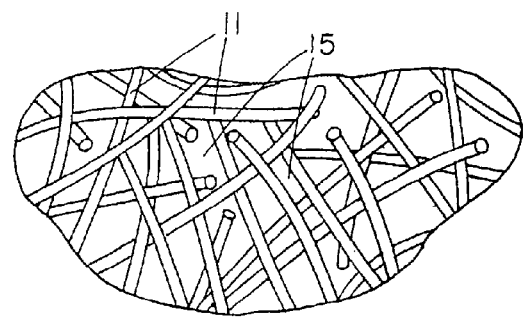
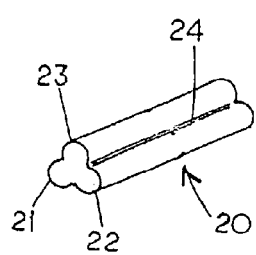
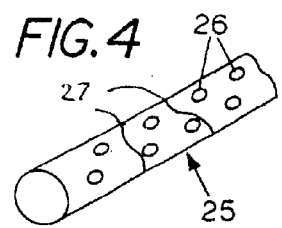

HEMOSTATIC MEDIA

CROSS REFERENCE TO RELATED APPLICATIONS

This application claims priority from provisional application 60/711,844 filed Aug. 26, 2005

FIELD OF THE INVENTION

The present invention relates generally to the field of inhibiting or stopping bleeding and, more specifically to acceleration of blood clot formation through application of a hemostatic fibrous media to a bleeding wound.

STATEMENT REGARDING FEDERALLY SPONSORED RESEARCH OR DEVELOPMENT

None

REFERENCE TO A MICROFICHE APPENDIX

None

BACKGROUND OF THE INVENTION

It has been recognized in the prior art that it is desirable to stop bleeding by applying materials to the wound or tissue which initiate or enhance blood coagulation. Such materials have included liquid glues (cyanoacrylate adhesives, gelatinous glues, UV curable polymers, etc.). Other materials which are made from human or animal blood components have been used but therefore are expensive to manufacture.

One method used to reduce bleeding involves initiating or accelerate blood clotting by applying hygroscopic porous particles directly to a wound. In this method the porous particles absorb the water from blood allowing the natural fibrinogens within the blood to coagulate, which results in a blood clot. The pore size of such particles should be such that water is able to be readily adsorbed by the particles, but the clot forming blood components (thrombin, fibrinogen, fibrin, platelets, etc.) are not. The size of the pores, therefore, should be less than 1 micrometer (1,000 nm) and preferably less than 0.1 micrometer (100 nm). The particles may be made of many different materials, although it is preferable that the materials be biocompatible and eventually absorbed by the body. Another method is described in U.S. Pat. No. 4,822,349 (Hursey) which describes the use of zeolites, or molecular sieves, for accelerating clotting. The zeolites are used in a particle form either as a powder poured onto or into a wound, or embedded in a wound dressing. However, while effective at adsorbing water from the blood and stopping bleeding, this method suffers from several major problems. Zeolites are inorganic and are not readily adsorbed by the body which creates significant difficulties in caring for the wound once the bleeding is stopped. The zeolite particles, which have been placed in the wound, must be debrided or scraped out of the wound once the bleeding has stopped. This can be very painful for the trauma victim. There is also a strong exothermic reaction when water is adsorbed into zeolites that can cause the temperatures at the wound site to reach 40° C. to 50° C. or higher which can burn the patient. Also a significant number of people can have allergic reactions to the zeolites. Another major concern is that the loose zeolite particles can become entrained in a blood vessel where they will continue to promote formation of clots. These small clots, which can then circulate in the blood system, can potentially cause embolisms, strokes, or other clot related problems. The U.S. Pat. No. 6,060,461 (Drake) describes the use of particles made of porous materials from within the classes of polysaccharides, cellulosics, polymers (natural and synthetic), inorganic oxides, ceramics, zeolites, glasses, metals and composites.

Polysaccharides are preferred because of their ready availability and modest cost. They are widely known to be biocompatible and are readily absorbed by the body over time. Polysaccharides can be provided as starch, cellulose, and even chitin. Chitin based wound dressings are provided under the trade name "Hemcon" and comprise chitin particles (from shrimp) embedded in a wound dressing. The particles can be applied in a powder form directly to the wound, or held in place on the wound. However, powders are difficult to apply, especially to wounds in which blood is flowing since the powders can be washed away with the flowing blood before clotting can be initiated.

A solution to problem of the powders washing away is described in the Hursey and Drake patents wherein they embed or attach the powders to a wound dressing. The wound dressing can take the form of a sheet or film in which the particles are adhered to or to the surface of fibers which make up woven or non-woven gauze-like fabric or sheet. The particles can also be interspersed with fibers, filaments or other particles in a self supporting structure, entangled within the fibrous elements of a net, web, fabric or sheet. However, both the biocompatible particles and the zeolite particles suffer the same problem in that they can become entrained in the blood vessels and cause clotting related problems in the blood vessels. While both of the Hursey and Drake patents describe the use of a dressing with the particles embedded or attached to a dressing for ease of application, there still exists the danger of the particles shedding from dressing and becoming entrained in the blood vessel and causing clotting within a blood vessel. In addition, the use of a dressing made of one material combined with the particles made of a different material increases problems of biocompatibility and absorption. It also increases the complexity of manufacturing and consequently manufacturing costs. The U.S. Pat. No. 3,620,218 (Schmitt) discloses a felt made of polyglycolic acid fibers which may be used as a hemostat. However, the felted fibers can float from a bleeding surface and are generally too porous.

The U.S. Pat. No. 3,937,223 (Roth) discloses an improvement upon 3,620,218 by compaction of the felt on at least one side to provide strength and rigidity to the felt as well as providing a smoother surface which can be drawn into close conformity to the wound and thus reduce pockets in the felt where blood or other fluids can accumulate. Roth uses filaments of about 0.5 to 12 deniers per filament (approximately 7 um to 34 um) and, conveniently, 2 to 6 deniers (approximately 14 um to 24 um) per filament. These fibers are quite large and stiff which creates large pores when made into a felt. To reduce the large pores one compresses the felt to smoothen the surface of the felt and to press the filaments closer together to create smaller pores between the fibers and thereby enhance hemostatic properties of the felt. However, even after compaction this technique suffers from the large open regions or void volume. When the filaments are compressed together, the void volume, or amount of open area between fibers, is greatly reduced. The amount of open area between fibers is important as the open area allows water to be wicked between the fibers, leaving behind platelets and other clotting agents, thus initiating the clotting process. The void volumes in compressed and calendared felts are typically less than 70% and usually less than 50%. The low void volumes in the felt reduces the hemostatic effectiveness of the compressed felts since the wicking of the water from the blood is a function of the surface area of fibers in contact with the blood and the capillary effect created by the pore size as well as the number of pores in the surface of the media. In addition, to the less than optimal hemostatic properties, the fibers in the felt which have not been compacted or embossed are not bonded to the other fibers.

In contrast to the prior art the present invention is to provide a biocompatible wound dressing which promotes clotting, reduces the risk of clot-promoting particles from entering the bloodstream, is easy to use, and is cost-effective to manufacture.

SUMMARY OF THE INVENTION

A wound dressing for enhancing blood clotting comprising a hemostatic fibrous media wherein surfaces of a hydrophilic microfiber or hydrophilic microfibers are arranged proximate to each other to form pores therebetween with the pore size sufficiently small to inhibit wicking platelets from a wound into the pores.

BRIEF DESCRIPTION OF THE DRAWINGS

FIG. 1 is a perspective view of a planarity of spaced apart hydrophilic fibers forming a homeostasis media;

FIG. 2 is a perspective view of a portion of the homeostatic media of FIG. 1;

FIG. 3 shows a perspective view of a hydrophilic fiber having a set of three longitudinally extending lobes; and FIG. 4 is a perspective view of a hydrophilic fiber having cracks and homeostatic particles embedded therein.

DESCRIPTION OF THE PREFERRED EMBODIMENT

FIG. 1 shows a perspective view of a wound dressing 10 comprised of a non-woven web of elongated hydrophilic microfibers 11 forming a homeostasis media having a backing 12 to enhance handling of the wound dressing. Backing 12, which is a convenience in handling, is optional and need not be used. The microfibers 11 can have a solid or micro porous surface. The microfibers can be formed into a non-woven wound dressing without the use of adhesives or other dissimilar materials. In the preferred embodiment, the microfibers are made of biocompatible polymeric materials, and formed directly into a non-woven sheet which can be used as a blood clot inducing wound dressing. The microfiber surfaces can be held together by pressue, bonded or fused together at contact regions between adjacent microfibers during the manufacturing process which inhibits the microfibers from shedding or falling into the wound during application of the wound dressing 11. Bonding the microfibers to each other to avoid shedding thus inhibiting or preventing contamination of the wound from individual microfibers.

The use of microfibers in the present invention allows the non-woven sheet to be very pliable and flexible which allows it to easily conform to the contour or shape of the wound site. As such the non-woven sheet may be made into various configurations for specific types of wounds such as wraps, pads, bandages, plugs, custom shapes or other configurations similar to conventional wound dressing. The present invention can be supplied as rolls, flat sheets or die cut pieces of various shapes and sizes. In addition, these non-woven sheet can be of various thicknesses depending on the needs of the application.

Microfiber bonding, can be accomplished by one or more methods known in art including but not limited to chemical, resin, thermal, pressure bonding. Bonding of fibers is accomplished when the fibers (which may be coated with a resin or uncoated) are in molten, semi-molten, or sticky state and touching. This may be accomplished during the manufacturing of the fibers or after by use of the methods known in the art for bonding polymers.

The microfibers 11 are made from a hydrophilic material to promote rapid wicking and drawing liquids from blood (i.e. water, plasma and serum) from blood at a wound site to concentrate platelets and clotting factors. In order to increase the wetability and wicking characteristics of the microfibers it is preferred that the surface tension of the microfibers be at least 50 dynes/cm, and preferably, greater than 70 dynes/cm. The microfibers are made from hydrophilic material, and preferably from polymers which are biocompatible and bioabsorbable. Suitable hydrophilic materials include polyglycolic acid, polylactic acid, and other polymers commonly used for sutures and other applications requiring bioabsorbable materials. In order to increase wetability of the hydrophilic materials the polymers can be modified by sulphonation, chemical addition, grafting, or other techniques used to modify polymers.

FIG. 2 shows an enlarged view of a portion of wound dressing 10 revealing individual microfibers 11 with open regions or pores 15 extending between adjacent microfibers. The microfibers 11 are secured to each other at contact regions between adjacent microfibers to form a self-adhering homeostasis media with the pores formed by the gaps between the microfibers. In general, the size of pores 15 of the homeostasis media should be small enough to prevent platelets from wicking into the media but allow blood liquid to wick into the media. By inhibiting or preventing platelets from wicking into the media causes the platelets and other clotting factors to accumulate and concentrate on the surface of the media and thus initiate the clotting process.

As platelets are approximately, 2 to 4 micrometers in diameter, the effective pore size of the hemostatic media should generally be less than 4 micrometers and, preferably, less than 2 micrometers in size to block or inhibit the platelets from entering the pores. In general the pore size of the hemostatic media made from microfibers is directly related to the diameter of the microfibers used. For example, to make a hemostatic media having a pore size of about 2 micrometers the average fiber size of the media are approximately 2 micrometers or less in diameter. In general, the microfibers 11 of the present invention are generally 7 to 34 times smaller in diameter than the fibers proposed by Roth U.S. Pat. No. 3,937,223 or Schmitt U.S. Pat. No. 3,620,218.

For a given mass of fibrous mat, smaller pore sizes can be achieved by using smaller fibers. Smaller fibers are advantageous for several reasons: 1) smaller fibers enable more surface area in given fibrous mat volume. 2) smaller fibers enable creation of smaller pores and 3) smaller fibers enable more open void volume for a given fibrous mat volume.

Since the surface area to volume ratio is proportional to 1/(fiber diameter), the larger the fiber diameter, the smaller the surface area to volume ratio. It is advantageous to have a large surface area to volume ratio for a hydrophilic microfiber as the rate of adsorption of blood liquid into a hydrophilic microfiber increases with increase surface area and smaller pores. At the same time, the small size pores are able to increase the capillary effect to allow wetable fluid to wick from the wound to the hydrophilic microfibers. At the same time the fluid is being wicked through the pores the small pore size of the homeostatic media inhibits or prevents platelets, red blood cells, and white blood cells in the blood from being passing into the homeostatic media. Consequently, the blood cells including platelets and clotting factors accumulate on the surface of the media and proximate the wound to initiate clotting of blood.

The microfibers in the present invention include fibers that are hydrophilic to cause wicking of the blood fluids (primarily plasma/serum) into the fibrous mat. The higher the fibers surface tension the greater the wetability and wicking tendency of the fibrous mat will be. It is advantageous to have fibers with a surface tension of at least 50 dynes/centimeter to readily wet the fibers and cause rapid and substantial wicking of the fluid into the fibrous mat.

While pore size and fiber surface tension are important factors in the promoting wicking and clotting, the pore size is related to the average fiber diameter. By having the average fiber diameter approximately the same size as the platelets or smaller the average fiber diameter of the fibrous mat can be less than 4 microns and preferably less than 2 microns and more preferably less than 1 micron.

If desired the fibrous mat can also include hemostatic particles such as starch, collagen, oxidized cellulose, or others known in the art. These particles can be embedded in the surface of the fibers or encapsulated within the fibers themselves.

If desired the fibrous mat can also include a hemostatic agents such as calcium, fibrinogen, thrombin, factor VII, factor VIII or others know in the art to accelerate clotting.

If desired, the surface area of the microfibers can be enhanced in several ways. For example, smaller diameter microfibers can be used or the microfibers can be made in non-circular shapes such as a microfiber having a cross section with 3 or more lobes as shown in FIG. 3. That is, microfiber 20 has a first longitudinal lobe 22, a second longitudinal lobe 23 and a third longitudinal lobe 24. The fold or recessed region 24 can provide a region for adding homeostatic agent thereto. Smaller diameter microfibers and microfibers having non-circular shapes provide greater surface area per unit volume as well as enhancing the wicking capabilities. If desired, the channels created by the lobes on the microfibers can also be used to retain hemostatic particles such as starch, collagen, oxidized cellulose, or others known in the art, or also hemostatic agents or clotting accelerators such as calcium, fibrinogen, thrombin, factor VII, factor VIII or others know in the art.

The surface area of the microfibers can also be enhanced by creating a three-dimension texture on the surface of the microfibers during the manufacture of the microfibers. The texture can take the form of impressions, dimples, cracks, or other geometric shapes. These cracks or impressions, which can extend deep into the fiber, increase the surface area even further, thus creating greater surface area and increased wicking capabilities. FIG. 4 shows a perspective view of a hydrophilic microfiber having a set of embedded particles 26 and a set of cracks or fissures 27 that further increase the exterior surface area of the hydrophilic fibers.

The methods of manufacturing of the present invention include one or more of those known in the art including but not limited to melt blown, thermal bonded, chemical bonded, resin bonded, spun bonded, spunmelt bonded, carded, air laid, wet laid, spunlaced, hydroentangled, electro-spinning process or processes.

The microfibers can be extruded through a small opening in a die as a molten polymer and can be stretched or attenuated by blowing high velocity air co-currently with the microfibers while they are still warm.

The Average Pore Diameter (viscous-flow-average) $D_p$ is equal to the square root of $$32*\mu*(Z*T)*(V/\epsilon)/\Delta P$$

Where:
$D_p$=Average pore diameter
$Z$=Media thickness
$T$=Tortuosity (assumed to be $1/\epsilon$ for the purposes of the invention)
$\epsilon$=porosity of the medium
$\mu$=viscosity
$V$=Face velocity
$\Delta P$=Pressure drop across the medium For example, the average pore diameter can be specified to be less than certain value. The average pore size necessary to stop or impede blood cells and to concentrate clotting factors at the surface of the fibrous mat should be less than 4 microns and preferably less than 2 micron and more preferably less than 1 micron.

The microfibers can also be formed by the extrusion of a solution a polymer and a solvent through small openings in a die. This type of extrusion lowers the viscosity of the polymer solution and makes it easier to manufacture smaller microfibers. High velocity air may also be used to stretch or attenuate the microfibers. The solvent is flashed off or extracted from the microfibers in a secondary process.

To enhance the surface area mechanical stresses or cracks on the surface of the microfibers can be made by secondary processes such as chemical etching, radiation, temperature fracturing, or other techniques known in the art.

If desired, hemostatic particles or hemostatic agents can be mixed in with the polymer prior to the extrusion process which results in the particles or agents being embedded within the microfibers. The addition of hemostatic particles or agents to the hydrophilic microfibers can further enhance clotting by increasing the water absorbing properties of the microfibers at the blood/fiber interface.

While not as desirable, the hemostatic particles or hemostatic agents can be embedded on the surface of the microfibers while the microfibers are being formed and are still semi-molten. Embedding hemostatic agents during formation of the microfibers is preferred over the use of adhesives, binders or other techniques used in the gauze/particle devices. In the embedding process the particles are embedded in the surface of the microfibers while the microfibers are in semi-molten condition. The embedding process causes the hemostatic particle or hemostatic agents to be physically retained without the use of binders, adhesives or other means once the polymer cools. The embedding during a semi-molten state of the polymer creates a firm grip on the particles and significantly lessens the chances of having the particles released from the surface or internal areas of the media matrix.

Thus in one embodiment a feature of the present invention is to provide a wound dressing which does not have loose particles, is made from microfibers which are secured to each other and have a pore size for enhancing blood clotting, has a high degree of open are so as to enhance clotting, is flexible and conforms to the wound site, is biocompatible and bioabsorable, can be made of only one material of construction (i.e. one polymer), and is easy and less costly to manufacture. Other embodiments of the wound dressing comprise a fibrous media wherein a surface of a single hydrophilic microfiber is arranged to form a set of pores in a fibrous media with the set of pores having a pore size sufficiently small to inhibit wicking platelets from a wound into the media via the set of pores while the hydrophilic microfiber enhances wicking of water threrethrough. In other embodiments the microfibers can be held proximate each other without adhesion to provide a mat that can inhibit wicking of a platelet from a wound into the mat.

We claim:

1. A wound dressing for enhancing the clotting at a wound comprising: a plurality of hydrophilic microfibers, said plurality of microfibers forming a mat, said plurality of microfibers forming open pores located between adjacent microfibers with each open pore having a pore size sufficiently small to inhibit wicking of a platelet away from a wound and into the mat while allowing ingress of plasma into said mat.

2. The wound dressing of claim 1 wherein the microfibers comprise a polymer.

3. The wound dressing of claim 2 wherein the polymer comprises a biocompatible polymer.

4. The wound dressing of claim 2 wherein the polymer is bioabsorbable.

5. The wound dressing of claim 2 wherein the polymer is polyglycolic acid.

6. The wound dressing of claim 2 wherein the polymer is polylactic acid.

7. The wound dressing of claim 1 wherein a hemostatic particles is embedded in the microfibers.

8. The method of claim 7 including the step of compressing the spaced apart hydrophilic fibers into a mat of self-adhering hydrophilic fibers before applying the spaced apart hydrophilic fibers onto the wound site.

9. The wound dressing of claim 1 where the microfibers are bonded to each other.

10. The wound dressing of claim 1 wherein an average pore size is less than 4 micrometers.

11. The wound dressing of claim 1 wherein an average pore size is less than 2 micrometers.

12. The wound dressing of claim 1 wherein an average pore size is less than 1 micrometers.

13. The wound dressing of claim 1 wherein the microfibers have a surface tension of at least 50 dynes/centimeter.

14. The wound dressing of claim 1 wherein the microfibers are flexible.

15. The wound dressing of claim 1 where the microfibers have a circular cross section shape.

16. The wound dressing of claim 1 where the surface of the microfibers includes irregularities to increase the surface area of the microfibers.

17. The wound dressing of claim 1 wherein the microfibers comprise extruded polymer microfibers.

18. The wound dressing of claim 1 which contains a hemostatic agent to enhance clotting.

19. The wound dressing of claim 1 wherein hemostatic particles are encapsulated within the microfibers.

20. A method of accelerating the clotting of blood at a wound site while minimizing the chances of contaminating the wound by holding a mat of hydrophilic fibers on the wound site sufficiently long to allow the plasma in the blood to wick into the hydrophilic fibers while inhibiting platelets from migrating into the mat and conforming the mat to the contour or shape of the wound site.

21. The method of claim 20 wherein the step of conforming the mat to contour or shape of the wound site comprises conforming a set of spaced apart hydrophilic fibers to the wound site.

22. A homeostasis media comprising a plurality of hydrophilic fibers forming a mat with the plurality of hydrophilic fibers forming open pores therebetween with the open pores having a dimension sufficiently small to inhibit blood platelets therethrough while allowing ingress of plasma into said mat to promote wicking of the blood platelets at a wound.

23. A wound dressing for enhancing blood clotting comprising a hemostatic fibrous media wherein a surface of a hydrophilic microfiber is arranged to form a set of open pores in the fibrous media with the set of open pores having a pore size sufficiently small to inhibit wicking platelets away from a wound and into the media via the set of pores while allowing ingress of plasma through the set of pores while the hydrophilic microfiber enhances wicking of water therethrough.

* * * * *